(12) United States Patent
Marugan et al.

(10) Patent No.: US 9,663,485 B2
(45) Date of Patent: May 30, 2017

(54) TOCOPHEROL AND TOCOPHERYL QUINONE DERIVATIVES AS CORRECTORS OF LYSOSOMAL STORAGE DISORDERS

(71) Applicant: The United States of America, as represented by the Secretary, Dept. of Health and Human Services, Washington, DC (US)

(72) Inventors: Juan Jose Marugan, Gaithersburg, MD (US); Wei Zheng, Potomac, MD (US); Jingbo Xiao, Rockville, MD (US); John McKew, Poolesville, MD (US)

(73) Assignee: The United States of America, As Presented by The Secretary, Department of Health and Human Services, Washington, DC (US)

( * ) Notice: Subject to any disclaimer, the term of this patent is extended or adjusted under 35 U.S.C. 154(b) by 7 days.

(21) Appl. No.: 14/442,637

(22) PCT Filed: Nov. 14, 2013

(86) PCT No.: PCT/US2013/070156
§ 371 (c)(1),
(2) Date: May 13, 2015

(87) PCT Pub. No.: WO2014/078573
PCT Pub. Date: May 22, 2014

(65) Prior Publication Data
US 2016/0207902 A1    Jul. 21, 2016

Related U.S. Application Data
(60) Provisional application No. 61/727,296, filed on Nov. 16, 2012.

(51) Int. Cl.
| | | |
|---|---|---|
| *A01N 43/16* | (2006.01) |
| *A61K 31/355* | (2006.01) |
| *C07D 311/58* | (2006.01) |
| *A61K 31/335* | (2006.01) |
| *A61K 31/35* | (2006.01) |
| *A61K 31/352* | (2006.01) |
| *A61K 31/353* | (2006.01) |
| *C07D 311/72* | (2006.01) |
| *A61K 31/122* | (2006.01) |
| *A61K 31/724* | (2006.01) |
| *C07C 50/02* | (2006.01) |
| *C07C 50/06* | (2006.01) |
| *C07C 50/24* | (2006.01) |

(52) U.S. Cl.
CPC .......... *C07D 311/58* (2013.01); *A61K 31/122* (2013.01); *A61K 31/335* (2013.01); *A61K 31/35* (2013.01); *A61K 31/352* (2013.01); *A61K 31/353* (2013.01); *A61K 31/355* (2013.01); *A61K 31/724* (2013.01); *C07C 50/02* (2013.01); *C07C 50/06* (2013.01); *C07C 50/24* (2013.01); *C07D 311/72* (2013.01)

(58) Field of Classification Search
None
See application file for complete search history.

(56) References Cited

U.S. PATENT DOCUMENTS

| | | |
|---|---|---|
| 6,008,245 A | 12/1999 | Brendel et al. |
| 6,071,953 A | 6/2000 | Lang et al. |
| 9,044,451 B2 | 6/2015 | Zheng et al. |
| 2010/0279413 A1* | 11/2010 | Fain .................... A61K 31/122 435/406 |

FOREIGN PATENT DOCUMENTS

| | | |
|---|---|---|
| WO | WO 2011/112679 | 9/2011 |
| WO | WO 2012/012473 | 1/2012 |

OTHER PUBLICATIONS

Stone et al. Journal of the National Cancer Institute (1997), vol. 89, pp. 1006-1014.*
Tafazoli et al. Chem. Res. Toxicol. (2005), vol. 18, pp. 1567-1574.*
Bascunan-Castillo et al. (2004) J. Appl. Genet. 45(4):461-467 "Tamoxifen and vitamin E treatments delay symptoms in the mouse model of Niemann-Pick C".
Davidson et al. (2009) PLoS ONE 4(9) "Chronic Cyclodextrin Treatment of Murine Niemann-Pick C Disease Ameliorates Neuronal Cholesterol and Glycosphingolipid Storage and Disease Progression".
Gille et al. (2010) Mol. Nutr. Food Res. 54:601-615 "Tocopheryl quinones and mitochondria".
Koyama et al. (1994) Chem. Pharm. Bull. 42(10):2154-2156 "Synthesis of Fluorine Analogs of Vitamin E. III.[1)] Synthesis of 2-[4,8-Dimethyl-12-(trifluoromethyl)tridecyl]-2,5,7,8-tetramethyl-6-chromanol and 2-[4,12-Dimethyl-8-(trifluoromethyl)tridecyl]-2,5,7,8-tetramethyl-6-chromanol".
Koyama et al. (1995) Chem. Pharm. Bull 43(9):1466-1474 Synthesis of Fluorine Analogs of Vitamin E. IV.[1)] Synthesis of Bis(trifluoromethyl)tocopherols[2)].
Müllebner et al. (2010) Chem. Res. Toxicol. 23:193-202 "Modulation of the Mitochondrial Cytochrome bc₁ Complex Activity by Chromanols and Related Compounds".
Narashima et al. (2008) Mol. Pharmacol. 74(1):42-49 "Niemann-Pick C1-Like 1 Mediates α-Tocopherol Transport".
Rosenbaum et al.(2010) PNAS Early Edition "Endocytosis of beta-cyclodextrins is responsible for cholesterol reduction in Niemann-Pick type C mutant cells".

(Continued)

*Primary Examiner* — Patrick Lewis
(74) *Attorney, Agent, or Firm* — Fenwick & West LLP

(57) ABSTRACT

The subject invention relates to improved tocopheryl quinone derivatives and tocopherol derivatives having improved pharmacokinetics in vivo that can, in some embodiments, be useful in the treatment of Lysosomal Storage Disorders, restoration of normal mitochondrial ATP production, modulation of intracellular calcium ion concentration and other treatments or therapies. The tocopheryl quinone derivatives and tocopherol derivatives have side chains that have terminally halogenated carbon atoms.

17 Claims, 8 Drawing Sheets

(56) References Cited

OTHER PUBLICATIONS

Yu et a. (2005) J. Biol. Chem. 280(12):11731-11739 "Altered Cholesterol Metabolism in Niemann-Pick Type C1 Mouse Brains Affects Mitochondrial Function".
PCT International Search Report & Written Opinion, International Application No. PCT/US2013/070156, dated May 16, 2014, 9 Pages.
PCT International Preliminary Report on Patentability, International Application No. PCT/US2013/070156, dated May 19, 2015, 6 Pages.
PCT International Search Report & Written Opinion, International Application No. PCT/US2011/044590, dated Jan. 12, 2011, 10 Pages.
PCT International Preliminary Report on Patentability, International Application No. PCT/US2011/044590, dated Jan. 22, 2013, 8 Pages.
State Intellectual Property Office, First Office Action, Chinese Patent Application No. 201380067222.9, dated Jun. 3, 2016, 9 Pages. (with English translation).
European Patent Office, Examination Report, European Patent Application No. 11741023.3, dated Nov. 6, 2013, 4 Pages.
European Patent Office, Examination Report, European Patent Application No. 11741023.3, dated May 28, 4 Pages.
European Patent Office, Examination Report, European Patent Application No. 11741023.3, dated May 19, 2015, 5 Pages.
European Patent Office, Examination Report, European Patent Application No. 11741023.3, dated Jul. 5, 2016, 4 Pages.
Bjorkhem, I., "Cerebrotendinous xanthomatosis," Curr. Opin. Lipidol, 2013, pp. 283-287, vol. 24.
Brigelius-Flohe, R., "Vitamin E: The shrew waiting to be tame," Free Radical Biology & Medicine, 2009, pp. 543-554, vol. 46.
Eng, C. M., et al., "Fabry disease: Guidelines for the evaluation and management of multi-organ system involvement," Genet. Med., 2006, pp. 539-548, vol. 8, No. 9.
Fechner, H., et al., "α- and δ-tocopherol induce expression of hepatic α-tocopherol-transfer-protein mRNA," Biochem. J., 1998, pp. 577-581, vol. 331.
Gullotta, F., et al, "Differentiation of Rare Leukodystrophies by Post-Mortem Morphological and Biochemical Studies: Female Adrenoleuko-dystrophy-Like Disease and Late-Onset Krabbe Disease," Neuropediatrics, 1996, pp. 37-41, vol. 27.
Helquist, P., et al., "Current Status of Drug Therapy Development for Niemann-Pick Type C Disease," Drugs of the Future, 2009, pp. 315-331, vol. 34, No. 4.
Jabs, S., et al., "Accumulation of bis(monoacylglycero) phosphate and gangliosides in mouse models of neuronal ceroid lipofuscinosis," Journal of Neurochemistry, 2008, pp. 1415-1425, vol. 106.
Liu, B., et al., "Reversal of defective lysosomal transport in NPC disease ameliorates liver dysfunction and neurodegeneration in the npc-1-/-mouse," Proc Natl Acad Sci, 2009, pp. 2377-2382, vol. 106, No. 7.
Marschner, K., et al., "A Key Enzyme in the Biogenesis of Lysosomes Is a Protease That Regulates Cholesterol Metabolism," Science, 2011, pp. 87-90, vol. 87.
McGlynn, R., et al., "Differential Subcellular Localization of Cholesterol, Gangliosides, and Glycosaminoglycans in Murine Models of Mucopolysaccharide Storage Disorders," The Journal of Comparative Neurology, 2004, pp. 415-426, vol. 480.
Micsenyi, M. C., et al., "Neuropathology of the Mcoln11-/-Knockout Mouse Model of Mucolipidosis Type IV," J. Neuropathol. Exp. Neurol., 2009, pp. 125-135, vol. 68, No. 2.
Platt, F. M., et al., "Treating lysosomal storage disorders: Current practice and future prospects," Biochimica et Biophysica Acta, 2009, pp. 737-745, vol. 1793, No. 4.
Sandhoff, K.,"Metabolic and cellular bases of sphingolipidoses," Biochemical Society Transactions, 2013, pp. 1562-1568, vol. 41, No. 6.
Sillence, D. J., "Glucosylceramide modulates endolysosomal pH in Gaucher disease," Molecular Genetics and Metabolism, 2013, pp. 194-200, vol. 109.
Solgar Natural Liquid Vitamin E., [online][Retrieved on Jul. 28, 2014] Retrieved from the Internet <URL: http://www.iherb.com/Solgar-Natural-Liquid-Vitamin-E-4-fl-oz-118-ml/9742>.
Sontag, T. J., et al., "Cytochrome P450 ω-Hydroxylase Pathway of Tocopherol Catabolism," The Journal of Biological Chemistry, 2002, pp. 25290-25296, vol. 277, No. 28.
Sontag, T. J., et al., "Influence of major structural features of tocopherols and tocotrienols on their ω-oxidation by tocopherol-ω-hydroxylase," Journal of Lipid Research, 2007, pp. 1090-1098, vol. 48.
Tucker, J. M., et al., "Alpha-tocopherol: roles in prevention and therapy of human disease," Biomedicine & Pharmacotherapy, 2005, pp. 380-387, vol. 59, No. 7.
Valenzuela, A., et al., "Differential Inhibitory Effect of alpha-, beta-, gamma-, and delta-Tocopherols on the Metal-Induced Oxidation of Cholesterol in Unilamellar Phospholipid-Cholesterol liposomes," J Food Sci, 2002, pp. 2051-2055, vol. 67, No. 6.
Valenzuela, A., et al., "Cholesterol oxidation: Health hazard and the role of antioxidants in prevention," Biol. Res., 2003, pp. 291-302, vol. 36.
Walkley, S. U., et al., "Abnormal neuronal metabolism and storage in mucopolysaccharidosis type VI (Maroteaux-Lamy) disease," Neuropathology and Applied Neurobiology, 2005, pp. 536-544, vol. 31.
Yamashita, K., et al., "Sesame Seed Lignans and γ-Tocopherol Act Synergistically to Produce Vitamin E Activity in Rats," The Journal of Nutrition, 1992, pp. 2440-2446.
Yates, A. J., et al., "Sudanophilic Leukodystrophy with Large Amounts of Cholesterol Ester," Neurochemical Pathology, 1983, pp. 103-123, vol. 1.

\* cited by examiner

FIG. 3A

| Sample | Tissues | | $CF_3$-tocopherol | | | | |
|---|---|---|---|---|---|---|---|
| animal # | wt | volume | 1st Anal | 2nd Anal | 3rd Anal | Average | Normalized |
| | mg | μL | ng/sample | ng/sample | ng/sample | ng/sample | μM |
| #1 | 5.90 | 5.90 | 11.4 | 18.7 | 13.1 | 14.4 | 5.21 |
| #2 | 4.12 | 4.12 | 26.2 | 34.9 | 26.5 | 29.2 | 15.13 |
| #3 | 4.98 | 4.98 | 39.8 | 45.5 | 39.9 | 41.7 | 17.89 |
| #4 | 4.94 | 4.94 | 19.7 | 21.5 | 15.5 | 18.9 | 8.17 |
| #5 | 6.47 | 6.47 | 44.9 | 36.9 | 26.9 | 36.2 | 11.95 |
| #6 | 4.79 | 4.79 | 26.9 | 32.1 | 27.1 | 28.7 | 12.79 |
| Average | | | | | | | 11.86 |

The molecular weight of $CF_3$-tocopherol is 468.5.
Diclofenac was used as the internal std.

*FIG. 5A*

| Sample animal # | $CF_3$-tocopherol mpk | Protein μg/μL | CE (16:0) ng/sample | Norm ng/mg | CE (18:0) ng/sample | Norm ng/mg | CE (18:1) ng/sample | Norm ng/mg | CE (18:2) ng/sample | Norm ng/mg | CE (20:4) ng/sample | Norm ng/mg |
|---|---|---|---|---|---|---|---|---|---|---|---|---|
| #1 | 300 | 8.34 | 6.40 | 15.3 | 2.64 | 6.33 | 9.69 | 23.2 | 2.71 | 6.50 | 11.20 | 26.9 |
| #2 | 300 | 7.95 | 8.19 | 20.6 | 2.39 | 6.01 | 7.58 | 19.1 | 1.98 | 4.98 | 8.40 | 21.1 |
| #3 | 300 | 7.00 | 8.36 | 23.9 | 2.51 | 7.17 | 8.01 | 22.9 | 2.40 | 6.86 | 7.50 | 21.4 |
| #4 | 300 | 8.53 | 14.60 | 34.2 | 3.49 | 8.18 | 10.30 | 24.2 | 3.23 | 7.57 | 12.50 | 29.3 |
| #5 | 300 | 8.97 | 7.52 | 16.8 | 1.57 | 3.50 | 8.44 | 18.8 | 2.40 | 5.35 | 12.00 | 26.8 |
| #6 | 300 | 8.70 | 7.45 | 17.1 | 3.33 | 7.66 | 7.22 | 16.6 | 1.87 | 4.30 | 10.30 | 23.7 |
| Average | | | | 21.3 | | 6.48 | | 20.8 | | 5.93 | | 24.9 |
| std error | | | | 2.9 | | 0.68 | | 1.2 | | 0.51 | | 1.3 |
| ttest | | | | 0.047 | | 0.011 | | 0.101 | | 0.184 | | 0.108 |
| #7 | control | 6.27 | 5.73 | 18.3 | 1.64 | 5.23 | 6.24 | 19.9 | 1.79 | 5.71 | 7.42 | 23.7 |
| #8 | control | 9.74 | 5.27 | 10.8 | 1.36 | 2.79 | 5.98 | 12.3 | 1.75 | 3.59 | 10.30 | 21.1 |
| #9 | control | 8.65 | 4.89 | 11.3 | 2.40 | 5.55 | 6.75 | 15.6 | 1.88 | 4.35 | 9.90 | 22.9 |
| #10 | control | 6.36 | 4.81 | 15.1 | 0.98 | 3.07 | 6.12 | 19.2 | 1.54 | 4.84 | 7.18 | 22.6 |
| #11 | control | 5.91 | 5.50 | 18.6 | 1.09 | 3.69 | 6.51 | 22.0 | 1.96 | 6.63 | 6.49 | 22.0 |
| #12 | control | 7.88 | 3.27 | 8.3 | 0.91 | 2.31 | 5.69 | 14.4 | 1.85 | 4.70 | 8.74 | 22.2 |
| Average | | | | 13.7 | | 3.77 | | 17.3 | | 4.97 | | 22.4 |
| std error | | | | 1.7 | | 0.54 | | 1.5 | | 0.44 | | 0.4 |

*FIG. 5B*

TOCOPHEROL AND TOCOPHERYL QUINONE DERIVATIVES AS CORRECTORS OF LYSOSOMAL STORAGE DISORDERS

PRIORITY DATA

This application is a 35 U.S.C. §371 national phase application of PCT/US2013/070156, filed Nov. 14, 2013, entitled "TOCOPHEROL AND TOCOPHERYL QUINONE DERIVATIVES AS CORRECTORS OF LYSOSOMAL STORAGE DISORDERS", which application claims the benefit of U.S. Provisional Application No. 61/727,296 filed on Nov. 16, 2012, entitled "TOCOPHEROL, AND TOCOPHERYL QUINONE DERIVATIVES AS CORRECTORS OF LYSOSOMAL STORAGE DISORDERS", all of which are hereby incorporated by reference in their entirety.

STATEMENT OF GOVERNMENT INTEREST

The instant application was made with government support; the government has certain rights in this invention.

RELATED APPLICATION DATA

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

FIELD OF THE INVENTION

The subject invention relates to novel tocopheryl quinone derivatives and tocopherol derivatives having improved pharmacokinetics in vivo that can, in some embodiments, be useful in the treatment of Lysosomal Storage Disorders, treatment of diseases caused by mitochondrial dysfunction, restoration of normal mitochondrial ATP production, modulation of intracellular calcium ion concentration and other treatments or therapies.

BACKGROUND OF THE INVENTION

A "Lysosomal Storage Disorder" or "LSD" is a disorder in which lysosomal function has been disrupted due to lysosomal enzymatic failure. There are approximately fifty LSDs, and all are rare inherited diseases in which genes for lysosomal proteins have been mutated. Individually, the frequency of each is less than 1:100,000, but collectively, the frequency is about 1:5,000-1:10,000. The defective enzyme can result in the accumulation of lipids, glycoproteins and mucopolysaccharides in the lysosome. LSDs include, without limitation, Niemann Pick Type C (NPC), Wolman, Niemann Pick Type A, Farber, Tay-Sachs, mucopolysaccharide IIIB (MSIIIB) and tripeptidyl-peptidase I (CLN2 or Batten) diseases.

LSDs are often fatal within a few months or years of birth. The symptoms include developmental delay, movement disorders, abnormal bone growth, pulmonary and cardiac problems, hepatomegaly, splenomegaly, dementia, seizures, blindness and/or deafness.

Intracellular vesicular traffic is integral to the operation of lysosomes and endosomes. The accumulation of undegraded substrates impacts the lysosome and endosome function. Lysosomes are involved in a number of cellular processes: phagocytosis, exocytosis, autophagy, immunity, receptor recycling, neurotransmission, signaling intracellularly, bone biology and pigmentation. Disruption in any one of these processes can have severe and usually fatal consequences (Parkinson-Lawrence, E. et al. (2010) Physiology 25:102).

A review of the LSDs and their associated clinical phenotypes has yielded generalizations regarding those phenotypes: 1) each disorder manifests a range of symptoms, which depend on the impact of the genetic mutation; 2) across disorders, there can be phenotypic similarities depending on the affected tissues and the similarity of the accumulated substrates; and 3) there can also be symptoms that distinguish the various disorders (Parkinson-Lawrence et al., supra).

There is no cure for LSDs. However, there is some therapy that has thus far demonstrated limited results in abatement of symptoms. Specifically, enzyme replacement therapy (ERT) and/or hematopoietic stem cell transplantation may be useful in slowing progression in certain types of LSDs (van Gelder, C M et al. (2012) Expert Opin. Pharmacother. 13(16):2281-99). Additionally, substrate reduction therapy and small molecule chaperones have been also proposed for the treatment of some LSDs.

The traditional accepted function of tocopherols is lipid antioxidants. Due to their physical characteristics and lipid solubility, tocopherols are mostly localized in membranes acting as radical quenchers, avoiding, for example, the oxidation of unsaturated phospholipids. The maintenance of membrane lipid composition and homeostasis is essential for proper function, transport, and protein docking. In the food industry, tocopherols are used to avoid oils becoming rancid.

Ubiquinione or Q10 is a fat-soluble, electron-transporting co-enzyme found in the electron-transport chain in mitochondria. Ubiquinone is a quinone which cyclically can change from an oxidized to a reduced form. Tocopheryl quinones act as poor mitochondrial decouplers, because they compete with Ubiquinione, inhibiting the transference of electrons between complex III and complex I and complex II. Alpha tocopheryl quinone has been used in human clinical trials for the treatment of Friedreich's ataxia, a mitochondrial disorder, with positive results of improving neurological function.

Bascuñan-Castillo et al. "Tamoxifen and vitamin E treatments delay symptoms in the mouse model of Niemann-Pick C," J. Appl. Genet. 45(4):461-7(2004), describe the improvement in lifespan and motor skills in NPC1 mice upon administration of α-tocopherol. Narashima et al. "Niemann-Pick C1-like 1 mediates alpha-tocopherol transport" Mol. Pharmacol. 74(1):42-9 (2008), describe studies demonstrating that α-tocopherol is absorbed in the intestine via the Niemann-Pick C1-like 1 (NPC1L1) transporter.

Koyama et al. "Synthesis of fluorine analogs of vitamin E. IV. Synthesis of bis(trifluoromethyl)tocopherols" Chem. Pharm. Bull 43(9):1466 (1995), describe synthesis of tocopherol analogues with a halogenated side chain or chromanol ring. Koyama et al. (1995) were studying the spin relaxation times (T$_2$) on fluorine NMR as an indication of how and where the analogues were incorporated into liposomes. Likewise, Koyama et al. "Synthesis of fluorine analogs of vitamin E. IIII. Synthesis of 2-[4,8-dimethyl-12-(trifluoromethyl)tridecyl]-2,5,7,8-tetramethyl-6-chromanol and 2-[4,12-dimemethyl-8-(trifluoromethyl)tridecyl]-2,5,7,8-tetramethyl-6-chromanol" Chem. Pharm. Bull 42(10): 2154 (1994), describe a tocopherol analogue with a halogenated side chain.

Takiguchi et al., U.S. Pat. No. 6,491,847, describe a quinone derivative having a benzoquinone core and R groups containing a halogenated side chain. These compounds were found to be useful as liquid crystal compounds because of their stable and broad discotic liquid crystal phase.

Gille et al. "Tocopheryl quinones and mitochondria," Mol. Nutr. Food Res. 54:601(2010), present evidence that tocopherol and α-tocopheryl quinone can alter mitochondrial respiration by inhibiting Complex III. Müllebner et al. "Modulation of the mitochondrial cytochrome bc1 complex activity by chromanols and related compounds," Chem. Res. Toxicol. 23(1):193-202 (2010), also demonstrate that tocopheryl quinones can inhibit mitochondrial electron transfer. Yu et al. "Altered cholesterol metabolism in Niemann-Pick Type C1 mouse brains affects mitochondrial function," J. Biol. Chem. 280(12):11731-39 (2005), teach that when the mitochondrial membrane potential is decreased, ATP synthesis is decreased.

There has also been research in relation to the treatment of LSDs with cyclodextrins. Rosenbaum et al., "Endocytosis of β-cyclodextrins is responsible for cholesterol reduction in Niemann-Pick type C mutant cells," PNAS Early Edition www.pnas.org/cgi/doi/10.1073/pnas.0914309107 (2010), describe studies that demonstrate that treatment of NPC cells with cyclodextrin results in enhanced exocytic transport of cholesterol to reduce cholesterol accumulation in those mutant cells. Davidson et al. "Chronic cyclodextrin treatment of murine Niemann-Pick C disease ameliorates neuronal cholesterol and glycosphingolipid storage and disease progression," PLoS ONE 4(9):e6951 (2009), describe chronic treatment of NPC mutant mice with cyclodextrin delayed clinical disease onset, delayed neurodegeneration, and increased lifespan.

Thus, there are studies that report that α-tocopherol, related compounds or cyclodextrin can improve LSD symptoms. Nonetheless, there continues to be a clear and urgent need for the development of further pharmaceutical agents for the treatment of LSDs.

SUMMARY OF THE INVENTION

The subject application provides novel tocopherol derivatives and tocopheryl quinone derivatives useful in the decrease of lysosomal substrate accumulation, the restoration of normal lysosomal size, and the treatment of lysosomal storage disorders (LSDs) and diseases associated with, resulting from, or caused by mitochondrial dysfunction. The novel derivatives can, in one embodiment, be metabolically stable.

In one embodiment, the subject invention comprises a tocopheryl quinone derivative with side chain modifications that, in some embodiments, confer improved pharmacokinetics. These compounds, in some embodiments, can exhibit the properties set forth herein, including, without limitation, modulation of mitochondrial potential, modulation of intracellular calcium ion concentration and restoration of some LSDs phenotypes. Also, the subject compounds and compositions, in a number of embodiments, can be used with cyclodextrins which will improve efficacy; in some cases, such improvement may be synergistic. The length of the aliphatic side chain is such that the compound's lipophilicity is maintained or augmented. Halogenation at the end of the compound (at the end of the side chain) can decrease the compound's ability to be oxidized. The side chain modification is typically terminal tri-halogenated methyl groups.

In another embodiment, the subject invention provides pharmaceutical compositions comprising the tocopheryl quinone derivatives and a pharmaceutically acceptable vehicle. The subject compound and/or compositions can be administered to individuals having LSD, or those who are otherwise in need thereof, to reduce symptoms related to impaired lysosomal lipid engorgement. The subject tocopheryl quinone derivatives at the proper dose can also improve mitochondrial ATP production, thereby restoring normal mitochondrial function.

The subject invention also provides a tocopheryl derivative having side chain modifications. The modifications are typically terminal tri-halogenated methyl groups. These compounds can manifest the properties described herein including, without limitation, improved lysosomal function, endosome-vesicle transfer and exocytosis, improved pharmacokinetics, and, when combined with a cyclodextrin, a synergistic effect.

In a further aspect, the invention includes a pharmaceutical composition comprising the subject tocopherol derivatives. This composition can be administered to individuals in need thereof, including those with LSD, for the improvement of lysosomal function and the treatment of associated diseases including LSD.

The compounds and compositions of the subject invention demonstrate a number of improvements over the prior art. In particular, the compounds and compositions can be found to reduce substrate accumulation in several LSDs relative to prior art compounds. There can be reduced pathological changes in the ultrastructure of LSD cells when observed with electron microscopy. They can also modulate intracellular $Ca^{2+}$ concentration and improve mitochondrial function.

The compounds and compositions of the subject invention can also demonstrate improved pharmacokinetics in biological samples and in vivo. The increased metabolic stability in vivo can improve central nervous system (CNS) penetration and exposure (by increasing the effective concentration of these compounds in the brain). Additionally, the increased lipophilicity of the subject compounds can increase membrane fluidity, thereby restoring lipid homeostasis and lysosomal size.

Finally, it has been found that when the subject compounds are used in combination with a cyclodextrin, the solubility of the subject compounds in aqueous mixtures or solutions is improved. As a result, the increased solubility can improve the efficacy of both the subject compounds and the cyclodextrin, resulting in enhanced lysosomal function. The use of cyclodextrin in combination with the subject compounds can produce a synergic effect. This effect in turn permits the reduction of dosage of both the subject compound and the cyclodextrin, thereby reducing side effects in an individual to whom the mixture has been administered. The foregoing improved properties can be detected or measured using methods known in the art.

BRIEF DESCRIPTION OF THE DRAWINGS

The following Detailed Description of the Invention, given by way of Examples, but not intended to limit the invention to specific embodiments described, may be understood in conjunction with the accompanying figures, in which:

FIG. 3A shows a table providing the results of a study of brain and plasma pharmacokinetics upon oral administration of X-analogue to Balb/c mice.

FIG. 5A shows a table providing the levels of $CF_3$-tocopherol NCGC00250218 in the brain of NPC mice at 72 h after 300 mg/kg single dose IP administration. FIG. 5B shows a table providing the levels of cholesterol esters in the brain of NPC mice before and after 72 h exposure to NCGC00250218 upon 300 mg/kg single dose IP administration.

DETAILED DESCRIPTION OF THE INVENTION

Figure 1A:
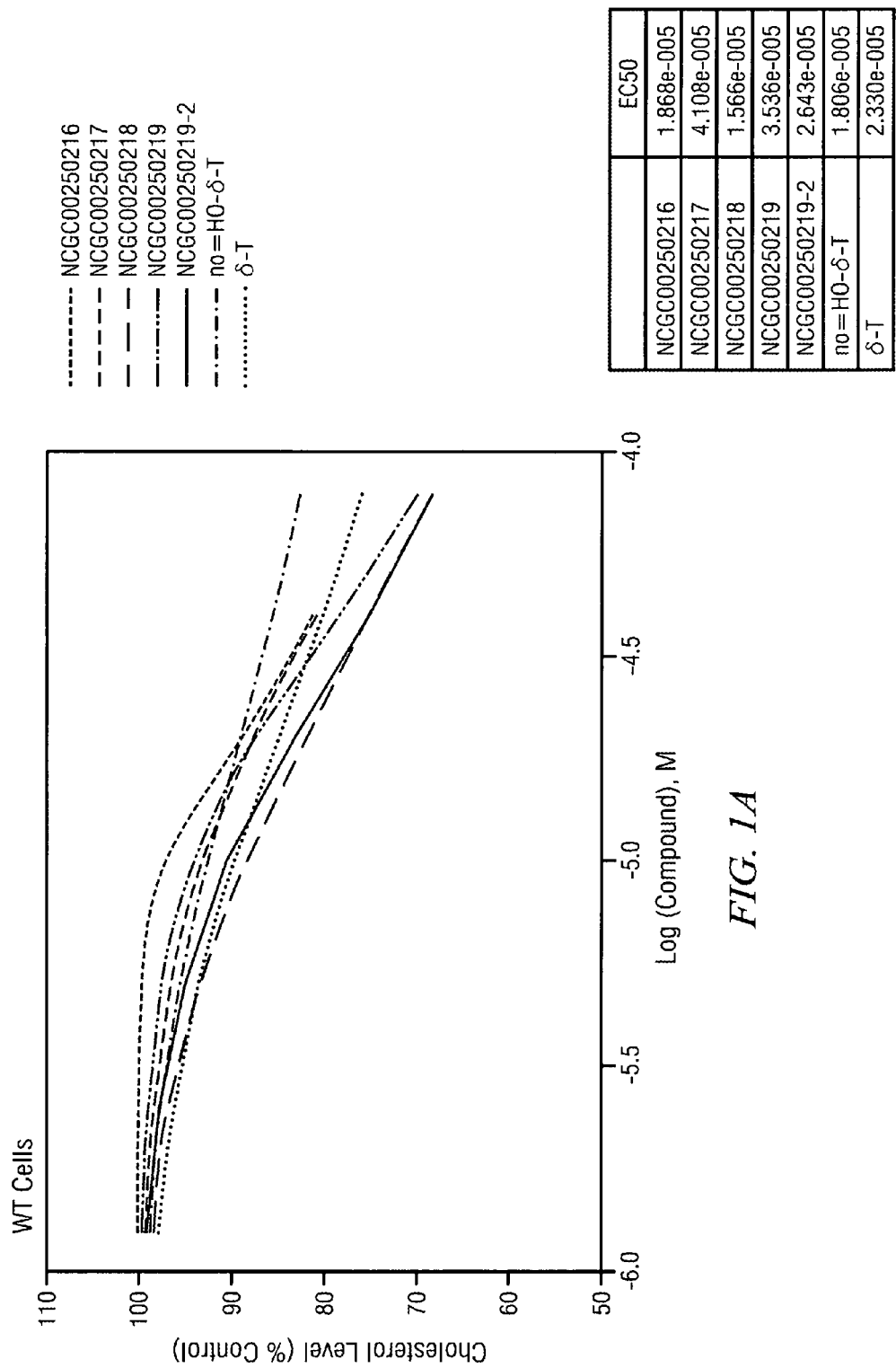
FIG. 1A shows a reduction of cholesterol levels in wild type cells upon treatment with delta tocopherol and analogues.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described herein.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference in their entirety and to the same extent as though each individual publication, published patent document, or patent application was specifically and individually indicated as being incorporated by reference in their entirety.

As used in this application, including the appended claims, the singular forms "a," "an," and "the" include plural references, unless the content clearly dictates otherwise, and are used interchangeably with "at least one" and "one or more."

As used herein, the term "about" represents an insignificant modification or variation of the numerical value such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

In the description that follows, a number of terms used in chemistry, medicine and biotechnology are used. In order to provide a clear understanding of the terms, the following definitions are provided.

As used herein, Lysosomal Storage Disorders or LSDs include, but are not limited to, the following disorders and diseases: Glycogen storage disease type II (Pompe disease), Mucopolysaccharidoses (MPS) (e.g., MPS types I-IV and VI-VII), Mucolipidoses (e.g., I-IV), Oligosaccharidoses (e.g., Schindler disease/Kanzaki disease, and alpha- and beta-mannosidoses), Lipidoses (e.g., Niemann-Pick disease types C and D, and Wolman disease), Sphingolipdoses (e.g., Niemann-Pick disease types A and B, Gaucher disease types I, II, and III, and GM1 and GM2 gangliosidoses including Tay-Sachs disease), and Lysosomal Transport diseases (e.g., Sialic acid storage disease).

Also contemplated for treatment employing the compounds of the invention are mitochondrial disorders and neurodegeneration. There are more than 40 distinct mitochondrial cytopathies including, without limitation, Friedreich's ataxia, Kearns-Sayre syndrome (KSS), Myoclonus epilepsy with ragged-red fibers (MERRF), Mitochondrial encephalomyopathy with lactic acidosis and stroke-like episodes (MELAS), Leber hereditary optic neuropathy (LHON), Leigh syndrome, Myoneurogenic gastrointestinal encephalopathy (MNGIE), Pearson syndrome, Neuropathy, ataxia, and retinitis pigmentosa (NARP).

An "individual" refers to a test subject or patient. The individual can be a mammal or a non-mammal. In various embodiments, the individual is a mammal. A mammalian individual can be a human or non-human. In various embodiments, the individual is a human. A healthy or normal individual is an individual in which the LSD disease is not detectable by conventional diagnostic methods.

NCGC00250218, X analogue, and $CF_3$-tocopherol are used interchangeably herein.

A "pharmaceutical composition" means a composition comprising a pharmaceutical agent, a pharmaceutically acceptable vehicle and optionally other components such as stabilizers, preservatives, pharmaceutically acceptable carriers and the like. The "pharmaceutical agent" is the tocopheryl quinone derivative and/or the tocopherol derivative described herein.

The pharmaceutical compositions of the subject invention can be prepared by known methods of combination of compounds in admixture with a pharmaceutically acceptable vehicle. Suitable vehicles and their formulation in pharmaceutical compositions are described in Remington's Pharmaceutical Sciences (16th ed. Osol, E. ed., Mack Easton Pa. (1980)). Essentially pure or pure pharmaceutical agents can be admixed with a pharmaceutically acceptable vehicle and other components to produce a pharmaceutical composition using current Good Manufacturing Practices.

An "essentially purified" agent is one that is substantially free from matter that is not of interest. With increasing preference, an essentially purified molecule is at least 80% pure, at least 90% pure, at least 95% pure, at least 97% pure, at least 98% pure, and at least 99% pure. A "pure" agent is one that has been purified to homogeneity, i.e., is 100% pure.

The invention includes essentially purified or pure tocopheryl quinone derivative and/or tocopherol derivative, and their inclusion in pharmaceutical compositions.

Additionally, stabilizers that can increase shelf life can be included in the pharmaceutical composition. Suitable stabilizers can include monosodium glutamate and 2-phenoxyethanol. Further, preservatives can be added so as to prevent contamination with bacteria and permit multidose vials. Suitable preservatives can include phenoxyethanol and formaldehyde.

A "pharmaceutically acceptable carrier" is slowly metabolized macromolecule including, without limitation, proteins, polysaccharides, polyglycolic acids, amino acid copolymers, and like carriers well known in the art.

"Pharmaceutically acceptable vehicle" refers to the water, saline, glycerol, ethanol, etc. used for dissolution, suspension, or mixing of components in the pharmaceutical composition.

The term "effective amount" or "therapeutically acceptable amount" for therapeutic treatment refers to an amount of agent sufficient to substantially improve lysosomal exocytosis in affected cells or tissues, and/or substantially improve clinical symptoms of the LSD at issue. It is believed that the effective amount(s) can be found within a relatively large, non-critical range. Routine experimentation can be used to determine appropriate effective amounts.

Methods of administration of a pharmaceutical composition of the subject invention to an individual can be carried out by any suitable means, including parenteral, e.g., intravenous, intradermal, intramuscular, subcutaneous, intranasal, intrathecal, transdermal (topical), transmucosal; and rectal and oral administration. In a preferred embodiment, the pharmaceutical composition is administered orally. In another embodiment, the pharmaceutical composition administered via infusion. In another embodiment, the pharmaceutical composition is injected directly into the central nervous system (CNS) to bypass the blood brain barrier.

The dosage administered depends on the route of administration. Generally, however, a dosage range of about 5 to about 300 mg/kg body weight of a subject can be useful. In one embodiment, the dosage range is about 10 to about 250 mg/kg. These dosage ranges (and others listed herein) include all of the dosage amounts around and between the stated values, including decimal values. Appropriate dosages can be determined using experimentation known to the technically skilled research scientist or clinician. Such determination may identify dosages outside of the stated ranges, which are also contemplated herein. For example, a single dosage may be about 1 mg/kg body weight.

"Cyclodextrins" are cyclic oligosaccharides used in pharmaceutical, drug delivery, food, agricultural and chemical industries, and environmental engineering. They are typically 6, 7 and 8-membered rings respectively denoted as α-, β- and γ-cyclodextrins. Cyclodextrin assists in moving cholesterol out of lysosomes in LSDs. Examples of cyclodextrins that could be suitable in the subject invention include, without limitation, hydroxypropyl β-cyclodextrin (HPBCD) and methyl-β-cyclodextrin (MβCD). In the subject invention, the hydrophobic cholesterol molecule lodges within the cyclodextrin ring which is then removed from the cell.

"Biological sample" means a fluid or tissue of an individual that commonly contains cells with impaired lysosomal function as evidenced by accumulation of substrate, enlarged liposomes and reduced mitochondrial ATP production. Biological samples include, without limitation, blood, plasma, serum, white blood cells, cerebral spinal fluid (CSF), myelomas, tears, saliva, milk, urine, lymph fluid, respiratory secretions, and genitourinary or intestinal tract secretions.

The subject invention provides, in one embodiment, a tocopheryl quinone derivative comprising a compound having structure [1]:

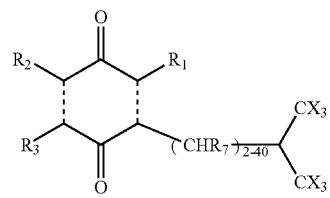

wherein the dotted line bonds indicate single or double bonds; $R_1$, $R_2$ and $R_3$=alkyl, fluoroalkyl, halogen or H; the side chain is an alkyl, alkenyl, or alkynyl chain, straight or branched, $R_7$=H or a single or double bond and X=a halogen.

The subject invention also includes a pharmaceutical composition that comprises the structure [1] compound and a pharmaceutically acceptable vehicle. The pharmaceutical composition comprising structure [1] can be used in a method of treating LSDs. In such method, the composition is administered to an individual in need thereof in a therapeutically effective amount.

In another aspect of the invention, the quinone derivative has structure [2]:

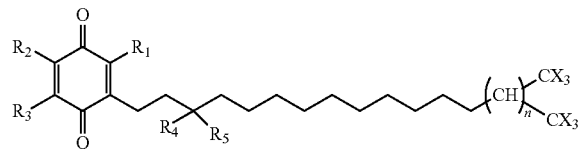

wherein $R_1$, $R_2$ and $R_3$=alkyl, fluoroalkyl, halogen or H; n=20; $R_4$, $R_5$=alkyl, fluoroalkyl, hydroxyl, alkoxy, or H; the side chain is an alkyl, alkenyl, or alkynyl chain, straight or branched and X=a halogen.

The subject invention also includes a pharmaceutical composition that comprises the structure [2] compound and a pharmaceutically acceptable vehicle. The pharmaceutical composition comprising structure [2] can optionally also include a cyclodextrin. The pharmaceutical composition can be used in a method of treating LSDs. In such method, the composition is administered to an individual in need thereof in a therapeutically effective amount.

Compounds having structures [1] and [2] can be used to improve mitochondrial ATP production. An improvement in ATP production can ameliorate the symptoms of certain LSDs. The function of the different complexes within isolated mitochondria and the final ATP production can be measured using, e.g., the XF CELL MITO STRESS TEST KIT® (Seahorse Bioscience).

In both of the compounds having structures [1] and [2], the terminal carbon has been halogenated. Typically, two branching tri-halogenated methyl groups are provided at the end of the side chain to substantially improved pharmacokinetics. Such compounds have been found to avoid hydrolysis and oxidation in the liver by the P450 isoform, CYP4F2.

In a further embodiment, the invention includes a tocopherol derivative having the structure [3]:

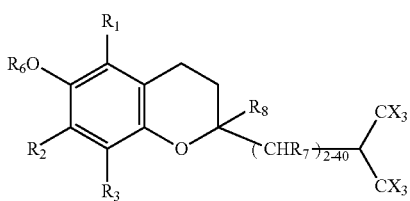

wherein $R_1$-$R_3$=alkyl, fluoroalkyl, halogen or H; $R_6$=alkyl, fluoroalkyl, alkenyl or H; $R_8$=a lower alkyl having $C_1$ to $C_6$; and the side chain is an alkyl, alkenyl, or alkynyl chain, straight or branched, wherein $R_7$=H or a single or double bond and X=a halogen.

The subject invention also includes a pharmaceutical composition that comprises the structure [3] compound and a pharmaceutically acceptable vehicle. The pharmaceutical composition comprising structure [3] can optionally also include a cyclodextrin. The pharmaceutical composition can be used in a method of treating LSDs. In such method, the composition is administered to an individual in need thereof in a therapeutically effective amount.

In a further aspect, the tocopherol derivative has structure [4]:

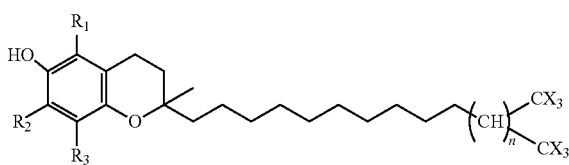

wherein $R_1$-$R_3$=alkyl, fluoroalkyl, halogen or H; n=1-20, the side chain is an alkyl, alkenyl, or alkynyl chain, straight or branched, and X=a halogen.

The subject invention also includes a pharmaceutical composition that comprises the structure [4] compound and a pharmaceutically acceptable vehicle. The pharmaceutical composition comprising structure [4] can optionally also include a cyclodextrin. The pharmaceutical composition can be used in a method of treating LSDs. In such method, the composition is administered to an individual in need thereof in a therapeutically effective amount.

In both of the compounds designated by structures [3] and [4], the terminal carbon has been halogenated. Typically, two branching tri-halogenated methyl groups are provided on the side chain to substantially improved pharmacokinetics. Such compounds have been found to avoid hydrolysis and oxidation in the liver by the P450 isoform, CYP4F2.

Treatment with the composition comprising the tocopheryl quinone derivative or tocopherol derivative comprising structures [1], [2], [3] or [4] can result in improvements that include, e.g., a substantial increase in $Ca^{2+}$ influx to the cells, lysosomal size reduction and/or an increment in cholesterol exocytosis from the cells of the patient, or otherwise provide improved properties as described herein.

Pharmaceutical Compositions

Once prepared, a compound of the invention in a pharmaceutically appropriate form and optionally including pharmaceutically acceptable carriers, excipients, diluents, complexation agents, or additives, will be administered to the patient requiring therapy and/or prophylaxis. Administration to patients can, for example, be via oral and/or parenteral administration routes. In certain embodiments, the compounds of the invention can be administered in any manner or employing any mode that will achieve effective concentrations of the compounds in the brain or central nervous system of the patient.

Thus, in one embodiment, the compound is formulated into a stable, safe pharmaceutical composition for administration to a patient. The composition can be prepared according to conventional methods by dissolving or suspending an amount of the compound ingredient in a diluent. The amount might be between about 0.1 mg and about 1000 mg per ml of diluent of the compound. A buffer may be added; optionally, a carbohydrate or polyhydric alcohol tonicifier and/or a preservative may also be added. Other excipients may also be present, if desired, to maintain the overall tonicity of the tocopherol derivative or other contemplated compound.

The terms buffer, buffer solution, and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. The stability of a formulation may be enhanced by maintaining the pH of the formulation in a range of approximately 5.0 to approximately 9.5. The buffer may, for example, be selected from an acetate buffer, a phosphate buffer, or a glutamate buffer.

Of greater relevance to a formulation comprising a compound of the invention for longer-term storage (i.e., with shelf-life in mind) is minimizing the Oxygen concentration. In one embodiment, Oxygen is essentially excluded from the formulation, so that reaction over time of the compound with oxygen cannot occur.

Carriers or excipients can also be used to facilitate administration of a compound according to the invention. Examples of carriers and excipients include, without limitation, calcium carbonate, calcium phosphate, various sugars such as lactose, glucose, or sucrose, or types of starch, cellulose derivatives, gelatin, polyethylene glycols, and physiologically compatible solvents.

A stabilizer may also be included in a pharmaceutical composition according to the invention. Exemplary stabilizers include carbohydrates and polyhydric alcohols.

A preservative may be added to a pharmaceutical composition described herein to inhibit microbial growth to avoid consequent spoilage of the composition by microorganisms. The amount of the preservative is not great, however, as it may affect the overall stability of the inventive compound. Preservatives, as well as each of the other components of pharmaceutical compositions are known in the art and are, for example, described in "Remington's Pharmaceutical Sciences" as well as Pharmaceutical Dosage Forms: Parenteral Medications, Vol. 1, 1992, Avis et al. Ed., Mercel Dekker, New York, N.Y. 1992, which is incorporated by reference in its entirety herein.

Pharmaceutically acceptable carriers, excipients, diluents, complexation agents, and/or additives may be chosen to enhance the stability of a compound according to the invention, facilitate synthesis or formulation of a pharmaceutical composition comprising the compound, and/or to enhance the bioavailability of the compound.

For example, carrier molecules such as cyclodextrin and derivatives thereof are well known in the art for their potential as complexation agents capable of altering the physicochemical attributes of drug molecules. For example, cyclodextrins may stabilize (both thermally and oxidatively), reduce the volatility of, and alter the solubility of, active agents with which they are complexed. Accommodation of one molecule within another is known as complexation and the resulting product is referred to as an inclusion complex.

Alternatively, the pharmaceutically appropriate form of the inventive tocopherol derivative compound may be formulated so as to enhance the stability and bioavailability of the compound.

One oral controlled release structure is enteric coating of a solid dosage form. Enteric coatings promote the compounds remaining physically incorporated in the dosage form for a specified period when exposed to gastric juice, yet the enteric coatings are designed to disintegrate in intestinal fluid for ready absorption. Delay of absorption is dependent on the rate of transfer through the gastrointestinal tract, and so the rate of gastric emptying is an important factor. For some administrations, a multiple-unit type dosage form, such as granules, may be useful.

Examples of preferred tocopherol derivative compounds of the present invention and/or compositions and/or complexes thereof exhibit advantageous pharmaceutical properties: they may be readily formulatable, are chemically and physically stable, readily water soluble, have low hygroscopicity, and/or exhibit good shelf life.

Aspects and embodiments of the present invention will now be described in the Examples. Further aspects and embodiments will be apparent to those skilled in the art.

EXAMPLES

Example 1

Synthesis of a Tocopherol Derivative

Step 1

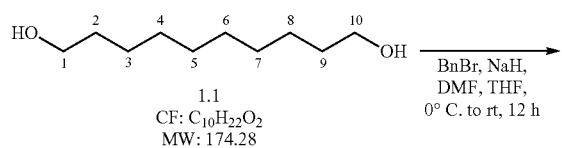

1.1
CF: $C_{10}H_{22}O_2$
MW: 174.28

BnBr, NaH,
DMF, THF,
0° C. to rt, 12 h

1.2
CF: $C_{17}H_{28}O_2$
MW: 264.40

Reaction Procedure:

To a 0° C. cooled solution of NaH (5.75 g, 143.67 mmol, 1 eq.) in dry DMF (100 mL), was slowly added compound 1 (25 g, 143.67 mmol, 1 eq.) in dry DMF (150 mL) at 0° C. and the resulting mixture was stirred 1 h at 0° C. After 1 h, benzyl bromide (20.62 ml, 172.41 mmol, 1.2 eq.) was added to the reaction mixture slowly drop-wise over a period of 20 min at 0° C. Then the reaction mixture was stirred at room temp for 12 h. After the completion of the reaction was checked by TLC, the reaction mixture was quenched in ice water and the aqueous layer was extracted with ether (2×30 mL). The combined organic extracts were dried over $Na_2SO_4$, filtered and concentrated under reduced pressure to obtain the crude product. The crude was purified by flash column chromatography over silica gel (100-200 mesh) by using 10% ethyl acetate in pet ether as eluent to obtain (23 g, yield—60%) of pure compound.

NMR data verified characteristics or properties of the step 1 compound (data not shown).

Step 2

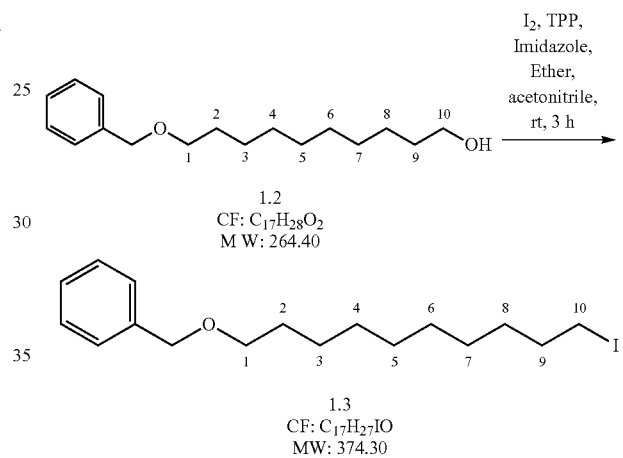

Reaction Procedure:

To a solution of compound 2 (25 g, 94.69 mmol, 1 eq.) in diethyl ether and acetonitrile (3:1 ratio) at 0° C., imidazole (9.02 g, 132.57 mmol, 1.4 eq.) and triphenyl phosphine (29.77 g, 113.63 mmol, 1.2 eq.) were added at 0° C. After 5 min stirring, iodine (31.26 g, 123.10 mmol, and 1.3 eq.) was added to the reaction mixture at 0° C. and the reaction mixture was stirred for 45 min at 0° C. After the completion of reaction was checked by TLC, the reaction mixture was filtered through celite bed and washed with diethyl ether. The filtrate was concentrated under reduced pressure to obtain the crude product. The crude was purified by flash column chromatography eluting with 2-3% ethyl acetate in pet ether to obtain (32.5 g, yield—92%) pure compound.

NMR data verified characteristics or properties of the step 2 compound (data not shown).

Step 3

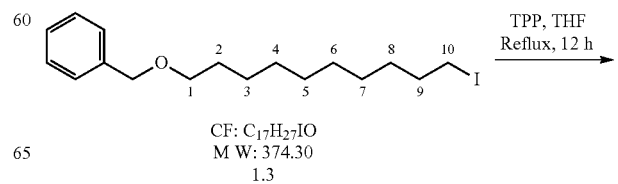

CF: $C_{17}H_{27}IO$
MW: 374.30
1.3

TPP, THF
Reflux, 12 h

-continued

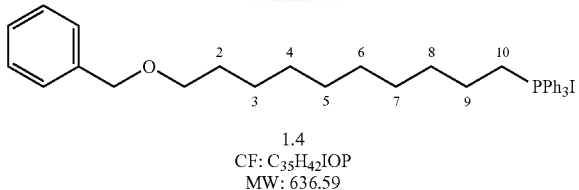

1.4
CF: C$_{35}$H$_{42}$IOP
MW: 636.59

Reaction Procedure:

To a solution of compound 3 (25 g, 66.84 mmol, 1 eq.) in dry THF, triphenyl phosphine (22.76 g, 86.89 mmol, and 1.3 eq.) was added. Then the reaction mixture was refluxed for 12 h. After the completion of reaction checked by TLC, the reaction mixture was distilled under reduced pressure and the crude compound was purified through flash column chromatography by using 5% methanol in dichloromethane as eluent to obtain (35.2 g, yield-83%) pure compound.

NMR data verified characteristics or properties of the step 3 compounds (data not shown).

Step 4

Reaction Procedure:

Compound 4 (50 g, 78.54 mmol, 1 eq) was taken in dry THF and cooled to −78° C., n-BuLi (103 ml, 164.9 mmol, 2.1 eq) was added drop-wise over a period of 1 h at −78° C. Hexafluoroacetone trihydrate (46 ml, 314.1 mmol, 4 eq) is added drop wise to conc. H$_2$SO$_4$. The gas hexafluoroacetone released was slowly purging into the above solution −78° C. The reaction mixture left for 12 h at room temperature. After completion of reaction, it was quenched with 2N HCl and the aqueous layer was extracted with ethyl acetate (2×300 mL). The combined organic extracts were dried over Na$_2$SO$_4$ and concentrated under reduced pressure to obtain the crude product. The crude was purified by flash column chromatography eluting with 5% ethyl acetate in pet ether to obtain (23.3 g, yield—75%) pure compound.

NMR data verified characteristics or properties of the step 4 compounds (data not shown).

Step 5

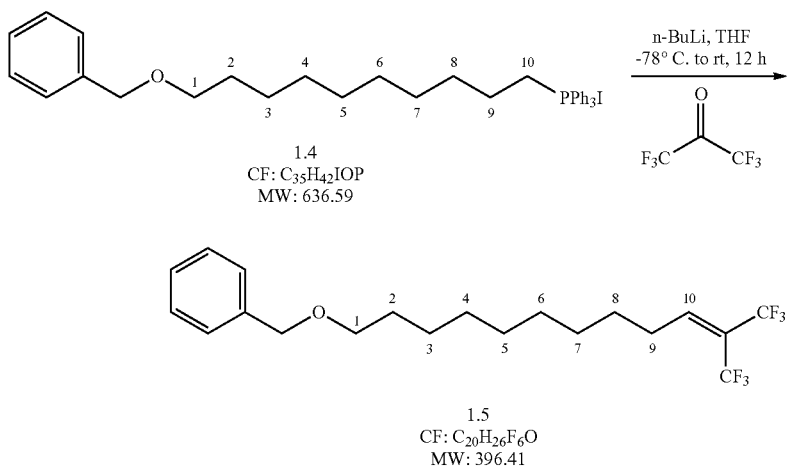

1.4
CF: C$_{35}$H$_{42}$IOP
MW: 636.59

1.5
CF: C$_{20}$H$_{26}$F$_6$O
MW: 396.41

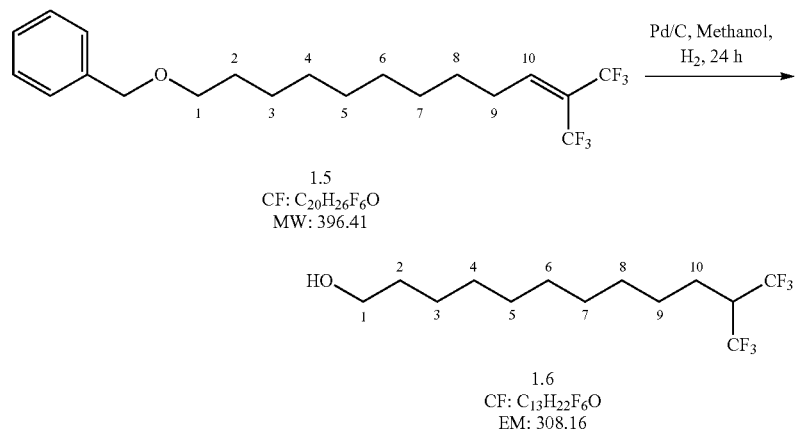

1.5
CF: C$_{20}$H$_{26}$F$_6$O
MW: 396.41

1.6
CF: C$_{13}$H$_{22}$F$_6$O
EM: 308.16

Reaction Procedure:

Compound 5 (25 g, 63.13 mmol, 1 eq) was taken in MeOH. Pd/C (10 g) was added portion wise under $N_2$. It was heated to 50° C., under 80 psi in par shaker apparatus for 24 h. After completion of reaction it was filtered through Celite, the filtrate was concentrated under reduced pressure to obtain the crude product. The crude was purified by flash column (100-200 silica gel) chromatography eluting with 2-3% MeOH in DCM to obtain (11 g, yield-85%) pure compound.

NMR data verified characteristics or properties of step 5 compounds (data not shown).

h at RT. After completion of reaction DCM was distilled off. The residue was dissolved in Diethyl ether and was filtered through celite. The filtrate was washed with sodium bicarbonate (2×300 ml). Organic extracts were dried over $Na_2SO_4$ and concentrated under reduced pressure to obtain (17.5 g, yield—88%) the crude product. The crude was itself taken to next step without further purification.

HPLC and NMR data verified characteristics or properties of the step 6 compounds (data not shown).

Step 7

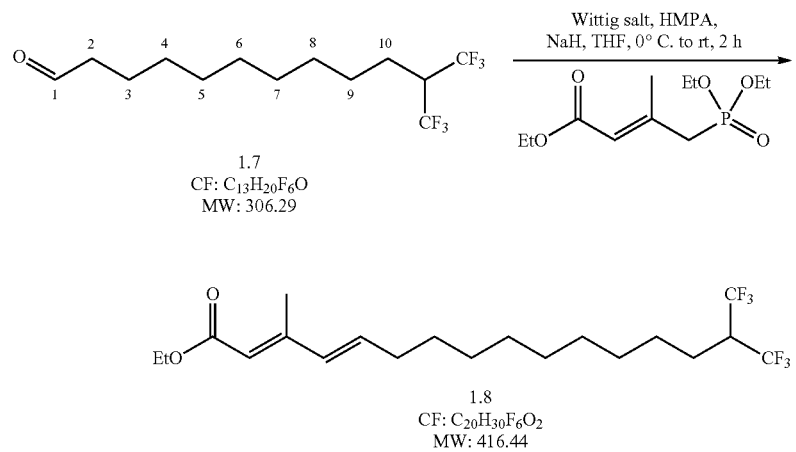

Step 6

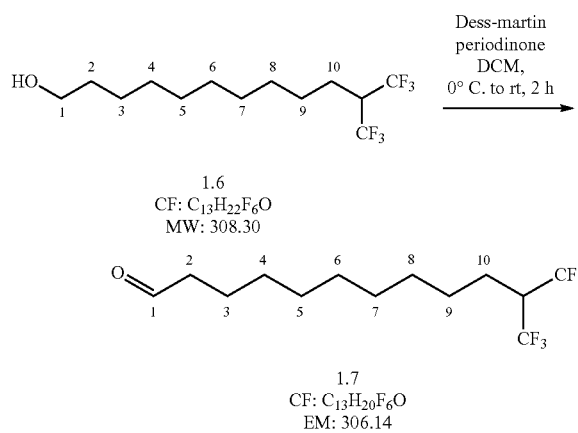

Reaction Procedure:

Compound 6 (20 g, 64.93 mmol, 1 eq) was taken in DCM and was cooled to 0° C., DMP (38.5 g, 90.90 mmol, 1.4 eq) was added portion-wise. The reaction mixture was left for 2

Reaction Procedure:

NaH (2.1 g, 86.192 mmol, and 2.2 eq) was added portion wise in THF at 0° C., then Wittig reagent (11.4 g, 43.095 mmol, 1.1 eq) was added drop-wise, and it was left for 1 h. Then HMPA (14 ml, 78.356 mmol, and 2 eq) and compound 7 (12 g, 39.178 mmol, 1 eq) in THF were added drop-wise at 0° C. The reaction mixture was left for 2 h at RT. After completion, the reaction was quenched with ice, extracted twice with diethyl ether and extracted with ether (2×30 mL). The combined organic extracts were dried over $Na_2SO_4$ and concentrated under reduced pressure to obtain the crude product. The crude was purified by flash column chromatography eluting with 10% ethyl acetate in pet ether to obtain (1.85 g, yield—65%) pure compound.

LCMS, HPLC and NMR data verified characteristics or properties of the step 7 compounds (data not shown).

Step 8

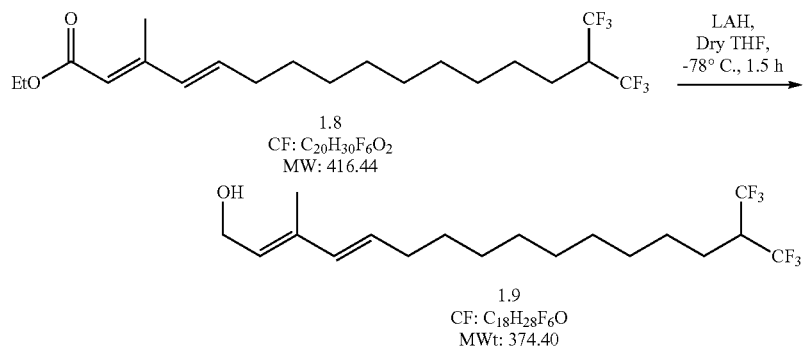

Reaction Procedure:

To a −78° C. cooled solution of Compound 8 (1 g, 2.4 mmol, 1 equiv) in dry THF (20 mL), was added LAH (4.8 ml, 1M solution, 2 equiv.) at −78° C., and the resulting mixture was stirred 3 h at −30° C. After the completion of the reaction was checked by TLC, a saturated solution of $NH_4Cl$ was added to the reaction mixture and the aqueous layer was extracted with ether (3×10 mL). The combined organic extracts were dried over $Na_2SO_4$ and concentrated under reduced pressure to obtained 0.8 g of compound 8 as colorless syrup. The obtained (0.75, yield—83%) crude was taken to next step without purification.

HPLC data verified characteristics or properties of the step 8 compound (data not shown).

Step 9

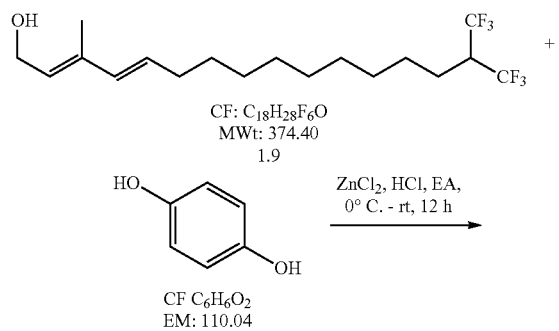

Reaction Procedure:

To a solution of Compound 9 (1 g, 2.67 mmol, 1 eq.) in EtOAc (20 mL), were added hydroquinone (0.29 g, 2.67 mmol, 1 eq.), zinc chloride (0.286 g, 2.13 mmol, 0.8 eq.), and HCl 37% aq (0.2 equiv) at 0° C. and the resulting mixture temperature was allowed to reach RT and maintained for 12 h at RT. After completion of the reaction was checked by TLC, a saturated solution of $NaHCO_3$ (10 mL) was added to the reaction mixture and the aqueous layer was extracted with ether (3×10 mL). The combined organic extracts were dried over $Na_2SO_4$ and concentrated under reduced pressure. The residue was purified by flash column chromatography on silica gel (hexane:EtOAc: 85:15) to give 0.25-0.3 g (75% LS-MS) of a brown syrup.

LCMS and NMR data verified characteristics or properties of step 9 compounds (data not shown).

Step 10

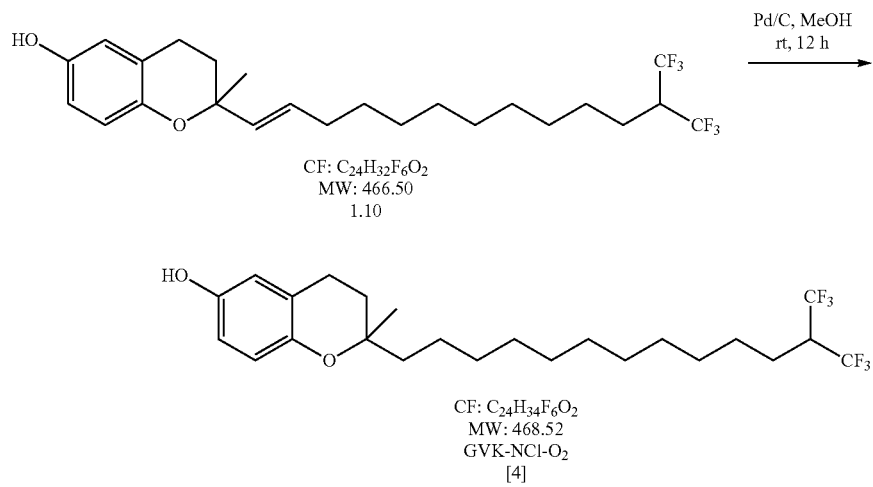

Reaction Procedure:

To a solution of Compound 10 (1 g, 2.14 mmol,) in methanol (20 mL), was added 10% Pd/C (0.25 g) and the resulting reaction mixture was stirred 12 h at hydrogen (balloon pressure) atmosphere. After completion of reaction was checked by mass spectrometry, the reaction mixture was filtered through celite bed, washed with methanol. The filtrate was concentrated under reduced pressure to obtained 0.8 g of compound GVK-NCI-02 as colorless syrup. The obtained crude was purified by prep HPLC to give (0.3 g, yield-30%) (95% HPLC) of light brown syrup.

HPLC and NMR data verified characteristics or properties of step 10 compounds (data not shown).

Example 2

Figure 1B:
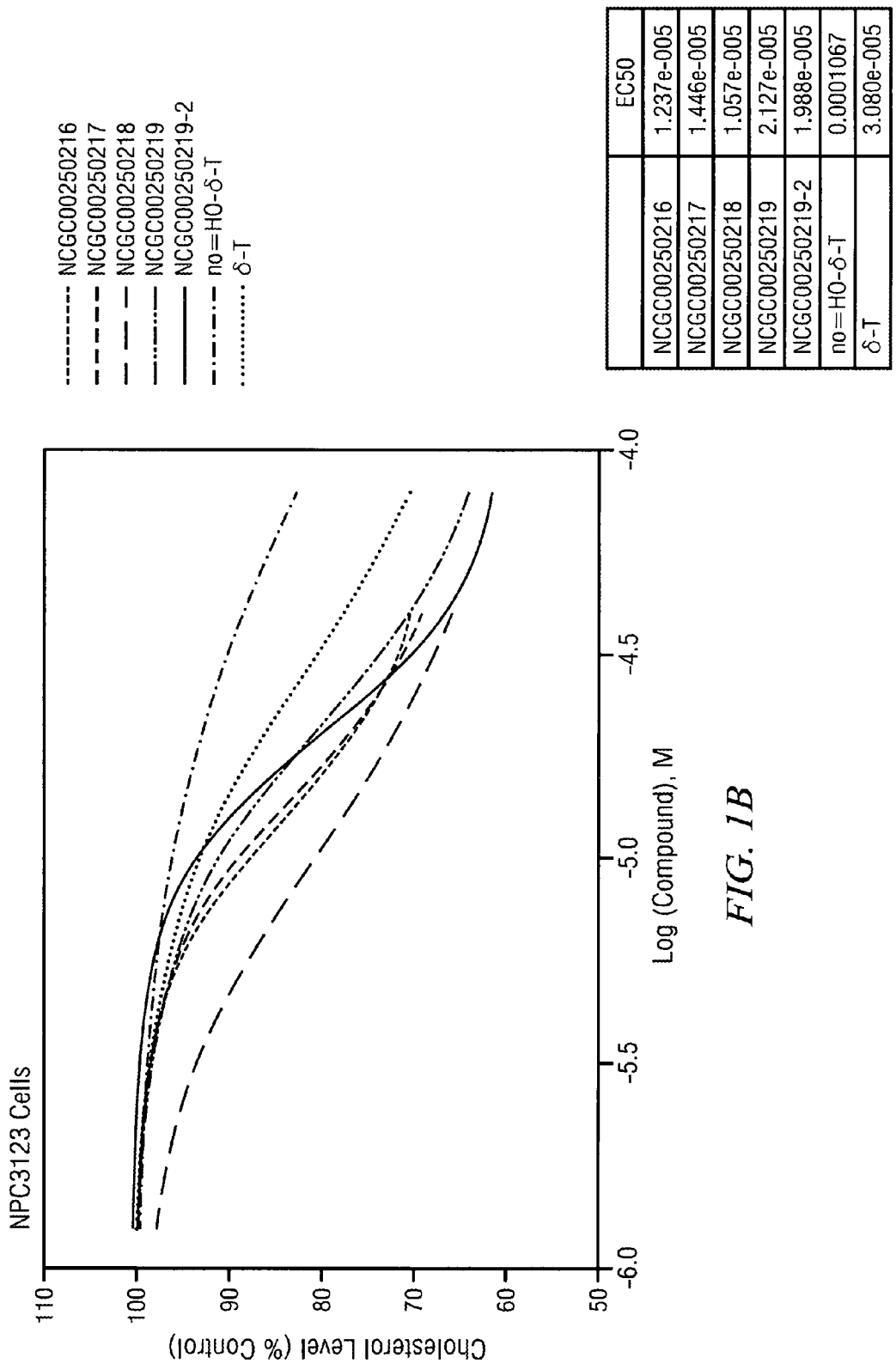
FIG. 1B shows a reduction of cholesterol levels in NPC fibroblasts upon treatment with delta tocopherol and analogues.
Figure 1C:
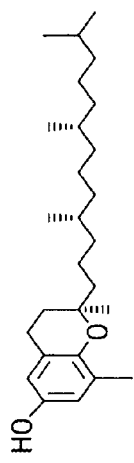
FIG. 1C provides the structures of a number of compounds (tocopherol analogues) tested (assayed in the NPC phenotypic assay).
Figure 1C:
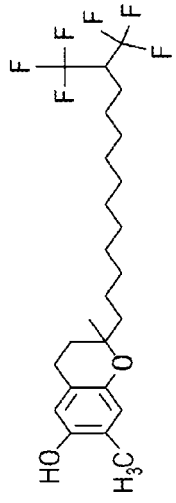
Figure 1C:
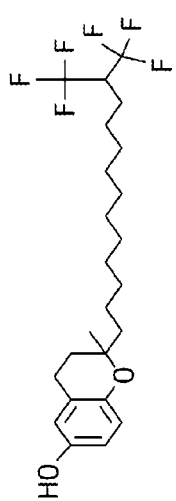
Figure 1C:
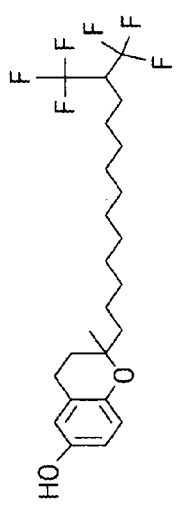
Figure 1C:
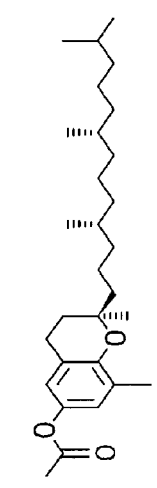
Figure 1C:
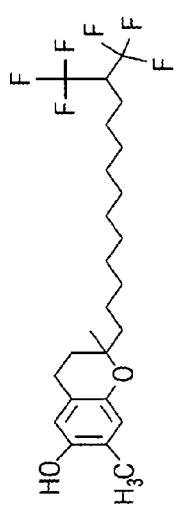

Reduction of Cholesterol Levels in Wild Type and in NPC Fibroblast Upon Treatment with Delta Tocopherol and Analogues The half maximal effective concentration (EC-50) for delta-tocopherol and five analogues was measured in wild type and NPC 3123 cells. FIG. 1A illustrates that as delta-tocopherol and analogue concentrations increased in wild type cells, serum cholesterol levels dropped. Further, in NPC cells (FIG. 1B), the cholesterol level drop was substantial relative to the control (no delta-tocopherol). The IC50 for phenotypic cholesterol elimination in NCP fibroblasts upon exposure to NCGC00250218 was in the range of 10 µM. The most significant change was seen with the "X-analogue" or NCGC00250218. Indeed, $CF_3$-tocopherol was more potent that delta-tocopherol (δ-T).

Example 3

Filipin Staining Assay for the Evaluation of Cholesterol Levels in Wild Type and in NPC Fibroblast Cells Upon Treatment with Delta-Tocopherol and NCGC00250218 (X-Analogue)

Figure 2:
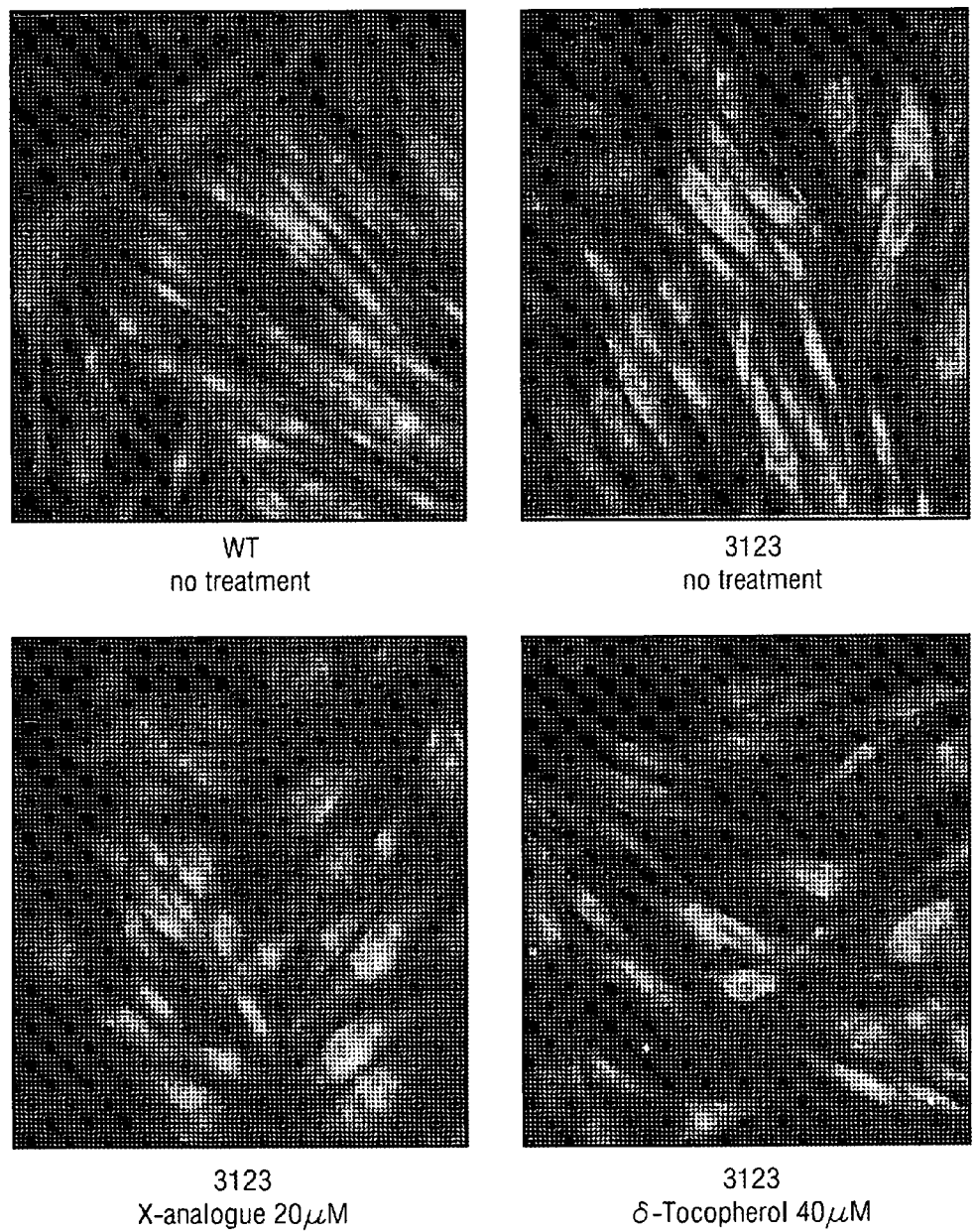
FIG. 2 shows the results of a Filipin staining assay for the evaluation of cholesterol levels in wild type and in NPC fibroblast upon treatment with delta tocopherol and NCGC00250218 (X-analogue).

Filipin, a histochemical dye for cholesterol, was used to detect cholesterol in wild type fibroblasts and NPC fibroblasts. Control fibroblasts, i.e., wild type and NPC fibroblasts, were treated only with filipin and no delta-tocopherol or analogues. Experimental samples were NPC cells that received either the X-analogue or delta-tocopherol. FIG. 2 shows that NPC cells treated with filipin and X-analogue (20 µM) have less cholesterol than NPC cells treated with filipin and delta-tocopherol (40 µM). Thus, treatment of NPC cells with X-analogue significantly reduces cholesterol level relative to cells treated with delta-tocopherol, even though the latter was used at double the concentration as the former.

Example 4

Figure 3A:
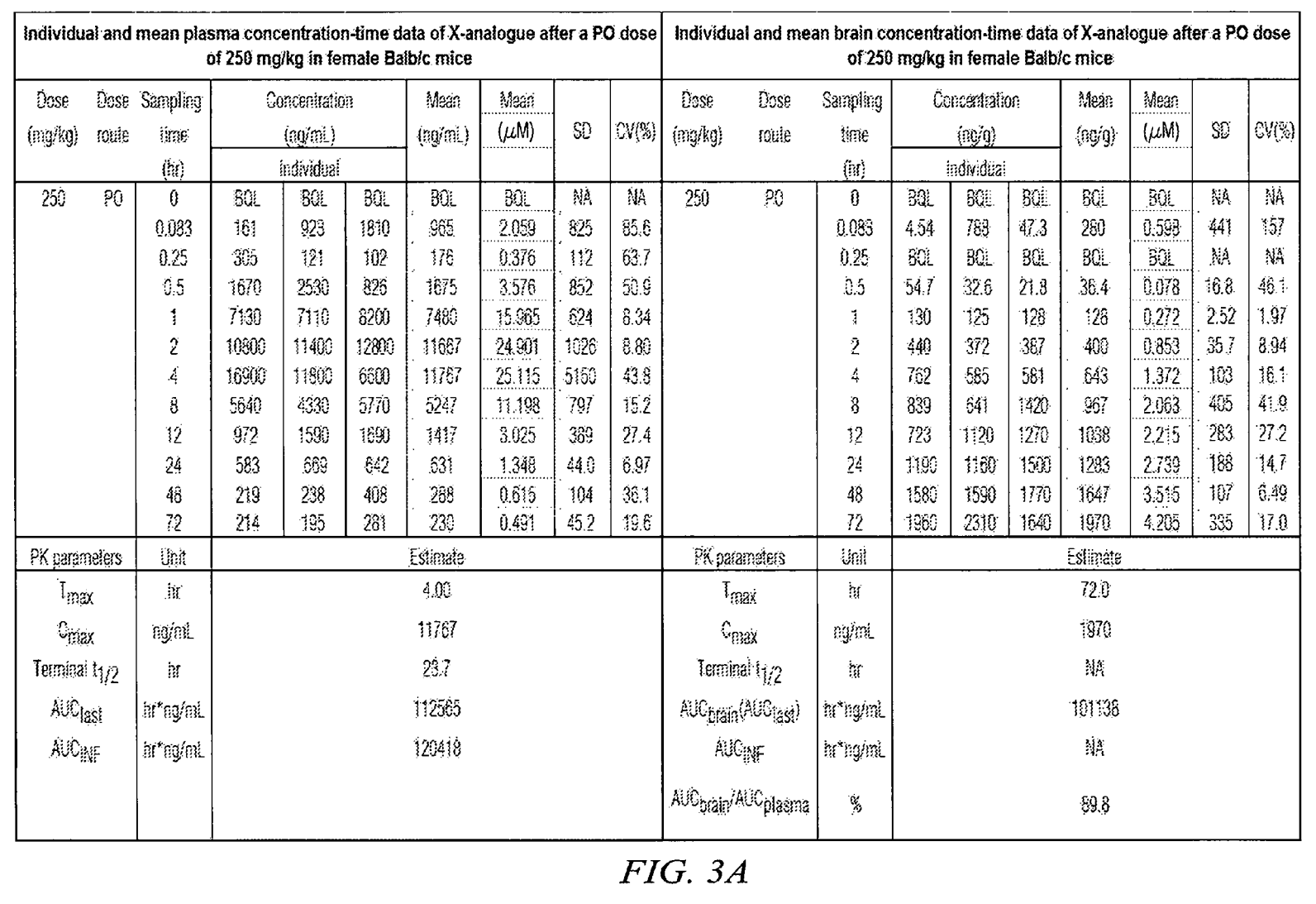
Figure 3B:
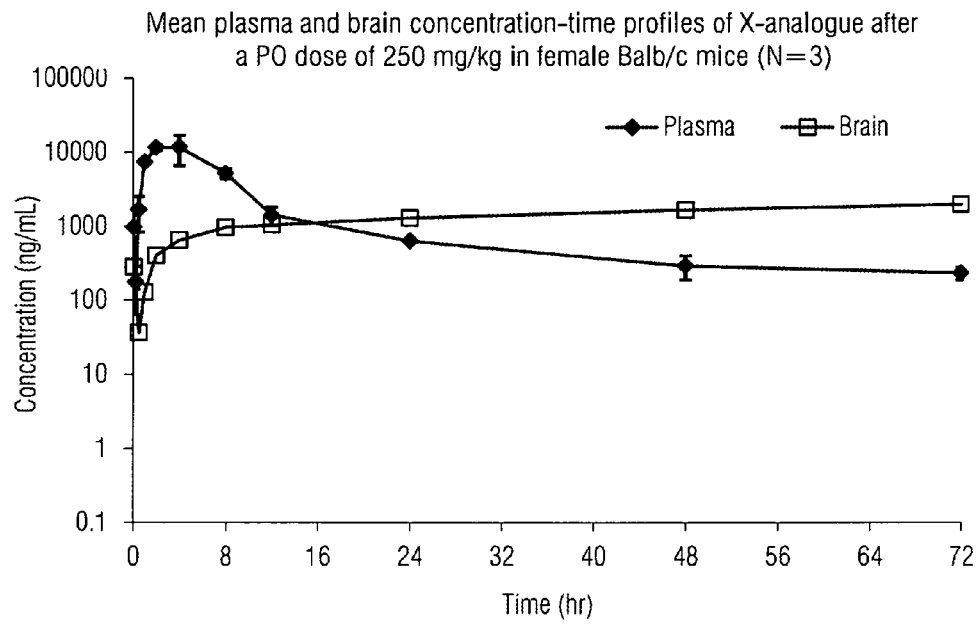
FIG. 3B depicts, in graph form, brain and plasma pharmacokinetics upon oral administration of NCGC00250218 (X-analogue).

Brain and Plasma Pharmacokinetics Upon Oral Administration of X-Analogue to Balb/c Mice The X-analogue was administered to female Balb/c mice so as to study time-concentration curves in brain and plasma. The FIG. 3A tables set forth the results. The peak mean concentration of X-analogue in serum occurs at approximately 2-4 hours; while the peak concentration in brain occurs at or after 72 hours. These results are also illustrated in the graph of FIG. 3B.

Example 5

Effect of Different Administration Routes and Doses for X-Analogue

Figure 4A:
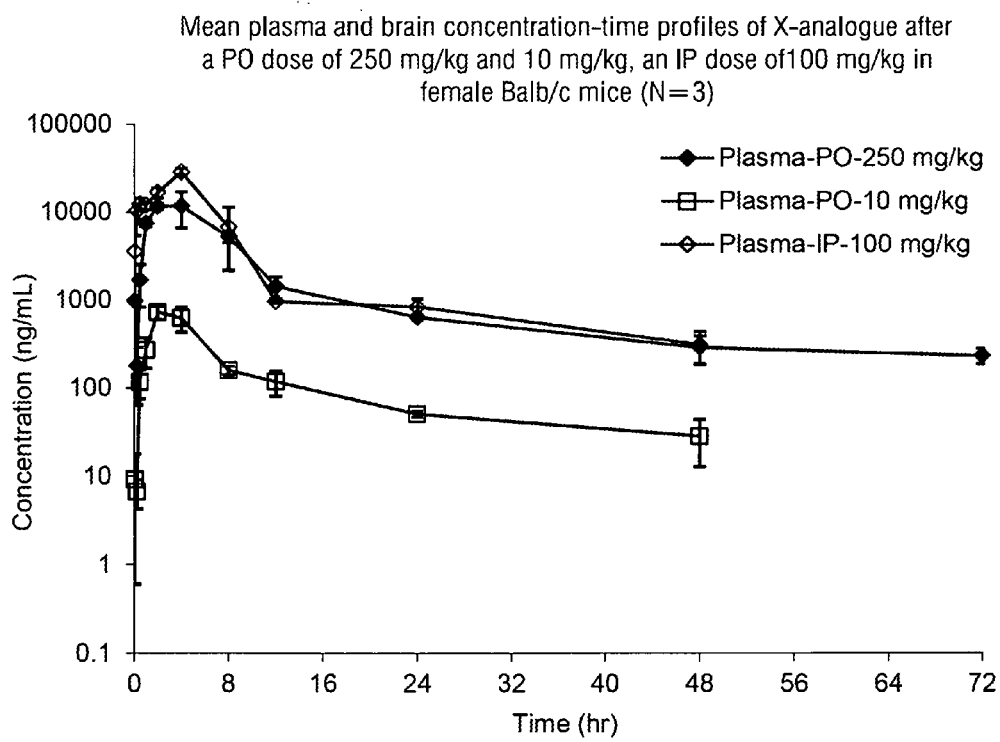
FIG. 4A depicts, in graph form, a mean plasma concentration-time profile comparison of different administration routes and doses for of NCGC00250218 (X-analogue).
Figure 4B:
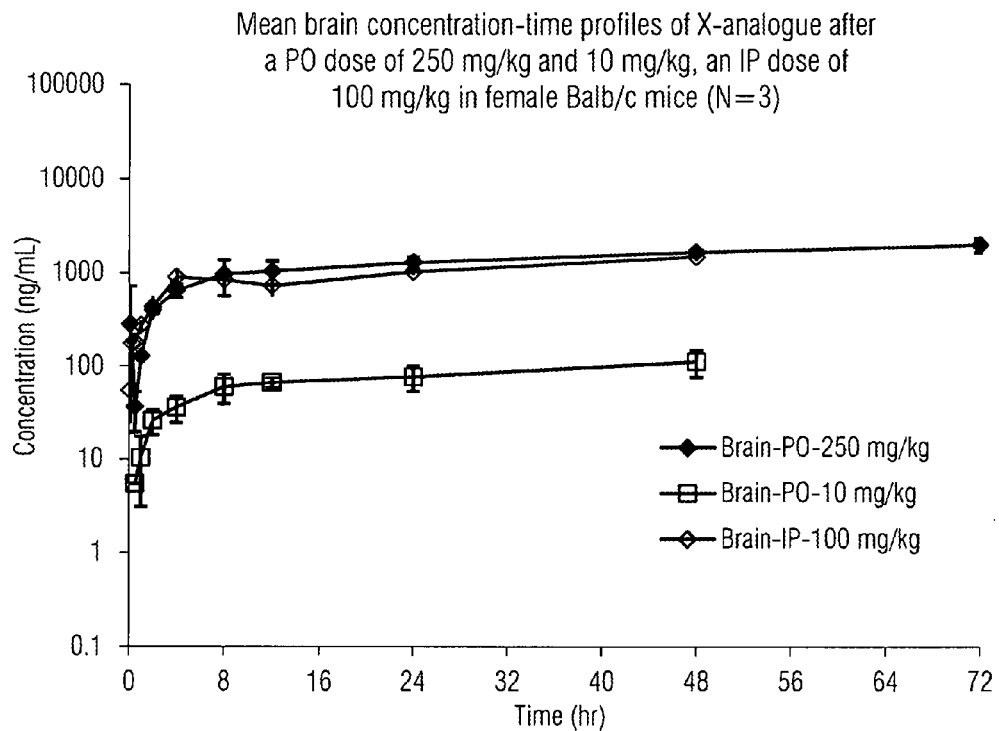
FIG. 4B depicts, in graph form, a mean brain concentration-time profile comparison of different administration routes and doses for of NCGC00250218 (X-analogue).
Figure 4C:
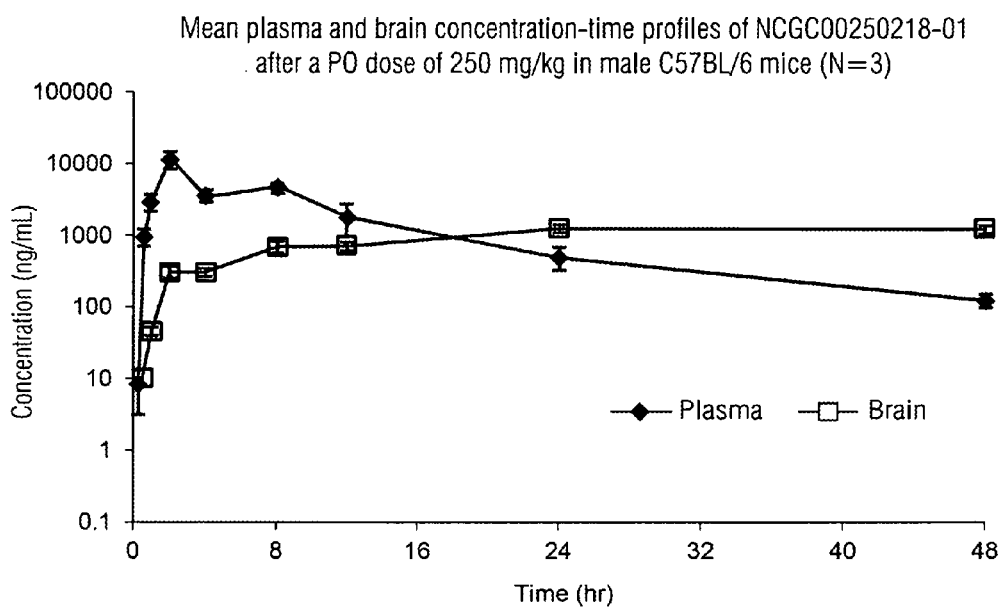
FIG. 4C shows the mean plasma and brain concentration-time profiles of NCGC00250218-01 after a per os (P.O.) (by mouth) dose of 250 mg/kg in male C5BL/6 mice.

The X-analogue was administered per os (PO) or intraperitoneal (IP) to female Balb/c mice so as to observe the effect in brain and plasma of administration route and dose. The results are set forth in FIGS. 4A, 4B, and 4C. In plasma (FIG. 4A), the PO route was seen to be more productive in generating a higher level of X-analogue. Surprisingly, the lower dose (10 mg/kg) of administered X-analogue produced a higher plasma concentration (ng/mL) than the higher dose (250 mg/kg). In brain (FIG. 4B), the PO route was again observed to be more productive in generating a higher level of X-analogue. The different doses (10 mg/kg and 250 mg/kg) for PO administration produced approximately the same brain concentration outcome. FIG. 4C shows the comparison of plasma vs. brain at 250 mg/kg. Thus, synthetic modulation of the aliphatic chain including $CF_3$-functional groups yielded molecules with improved pharmacokinetics. Of note, natural enzymes do not have the capacity to oxidize fluoroaliphatic chains.

Initial in vivo studies indicated that a single administration of $CF_3$-tocopherol (NCGC00250218) in Niemann Pick C mice elevates the production of cholesterol esters in the brain, which constitutes a sign of restoration of cholesterol homeostasis. Furthermore, a long-term pharmacokinetic study (up to 42 days after single I.P. dose of 100 mg/kg) has been completed (data not shown).

Example 6

Exposure to the CF3-Tocopherol NCGC00250218 Activates Cholesterol Metabolism

Like other natural occurring tocopherols, NCGC00250218 is most likely to have good bioavailability, but, for easy handling of NPC mice and for comparison of brain levels with previous pharmacokinetics experiments, I.P. administration was carried out. Based on previous experience with HPCD, compound and cholesterol-ester levels were measured after 72 hours exposure. It was found that exocytosis of lysosomal trapped cholesterol activates cholesterol metabolism increasing levels of cholesterol esters in brain and 24-hydroxycholesterol in plasma. A dose of NCGC00250218 was selected that would allow reaching brain concentrations similar to its IC50 in fibroblast (~10 µM). The results are shown in FIGS. 5A and 5B.

Additional studies with NCGC00250218 can be carried out to evaluate the kinetics of cholesterol turnover, measuring the elevation of cholesterol esters at 24 and 48 hours after 300 mg/kg single dose IP administration. Furthermore, the dose can be reduced to determine the minimum dose of NCGC00250218 that will produce cholesterol turnover. These results, together with the long term pharmacokinetic studies described, allow neurodegenerative and survival studies.

Studies described herein, thus, show that $CF_3$-tocopherol: decreases cholesterol accumulation in NPC patient cells (fibroblast and neurons); reduces enlarged lysosome in NPC cells; increases intracellular $Ca^{2+}$ and enhances lysosomal exocytosis; shows cholesterol metabolism turnover in NPC mice upon single administration; and has good brain penetration and an exceptionally long half-life (about 20 to 30 days). Indeed, the long half-life of $CF_3$-tocopherol allows the compound to reach the brain. It also allows for the possibility of administration over time—via infusion, for example, or low (micromolar range) daily, weekly, or even monthly oral concentrations. Thus, $CF_3$-tocopherol can be orally bioavailable and safe (based on large daily dosing in a rat model, up to 5 g/kg, without measurable or observable side effects). It is not metabolized as quickly.

$CF_3$-tocopherol (and $CF_3$-tocopheryl quinone) have potential applications in mitochondrial disorders and lysosomal storage diseases and neurodegeneration.

What is claimed is:

1. A compound of formula I:

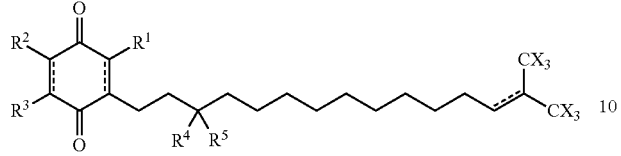

where
X is a halogen;
$R^1$, $R^2$ and $R^3$ are each independently selected from the group consisting of halogen, hydrogen, $C_1$-$C_6$ alkyl, and $C_1$-$C_6$ fluoroalkyl;
$R^4$ and $R^5$ are each independently selected from the group consisting of hydrogen, hydroxyl, $C_1$-$C_6$ alkoxyl, and $C_1$-$C_6$ alkyl; and
wherein === represents either a C-C single bond or a C=C double bond.

2. A compound of formula II:

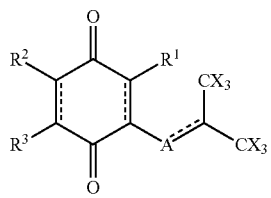

where
X is a halogen;
$R^1$, $R^2$ and $R^3$ are each independently selected from the group consisting of halogen, hydrogen, $C_1$-$C_6$ alkyl, and $C_1$-$C_6$ fluoroalkyl;
A is selected from the group consisting of $C_1$-$C_{40}$ alkyl, substituted $C_1$-$C_{40}$ alkyl, $C_2$-$C_{40}$ alkenyl, substituted $C_2$-$C_{40}$ alkenyl, $C_2$-$C_{40}$ alkynyl, and substituted $C_2$-$C_{40}$ alkynyl; and
wherein each and any substituted functional group may be substituted with up to three substituents and each substituent is selected from the group consisting of $C_1$-$C_6$ alkyl, $C_2$-$C_6$ alkenyl, and $C_2$-$C_6$ alkynyl;
and wherein === represents either a C-C single bond or a C=C double bond.

3. A compound of formula III:

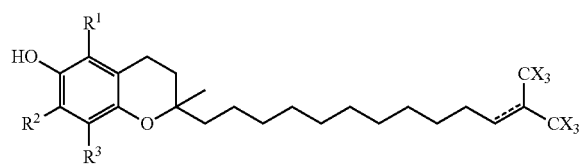

where
X is a halogen;
$R^1$, $R^2$, and $R^3$ are each independently selected from the group consisting of halogen, hydrogen, $C_1$-$C_6$ alkyl, and $C_1$-$C_6$ fluoroalkyl; and wherein === represents either a C-C single or a C=C double bond.

4. A compound of formula IV:

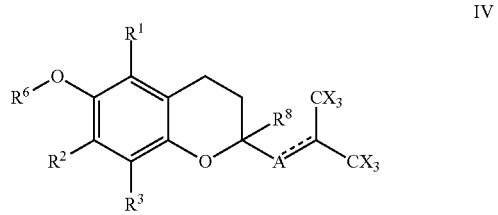

where
X is a halogen;
$R^1$, $R^2$, and $R^3$ are each independently selected from the group consisting of halogen, hydrogen, $C_1$-$C_6$ alkyl, and $C_1$-$C_6$ fluoroalkyl;
$R^6$ is selected from the group consisting of hydrogen, $C_1$-$C_6$ alkyl, $C_2$-$C_6$ alkenyl, and $C_1$-$C_6$ fluoroalkyl;
$R^8$ is a $C_1$-$C_6$ alkyl;
A is selected from the group consisting of $C_1$-$C_{40}$ alkyl, substituted $C_1$-$C_{40}$ alkyl, $C_2$-$C_{40}$ alkenyl, substituted $C_2$-$C_{40}$ alkenyl, $C_2$-$C_{40}$ alkynyl, and substituted $C_2$-$C_{40}$ alkynyl; and
wherein each and any substituted functional group may be substituted with up to three substituents and each substituent is selected from the group consisting of: $C_1$-$C_6$ alkyl, $C_2$-$C_6$ alkenyl, and $C_2$-$C_6$ alkynyl;
and wherein === represents either a C-C single or a C=C double bond.

5. The compound of claim 3 having the structure of formula V:

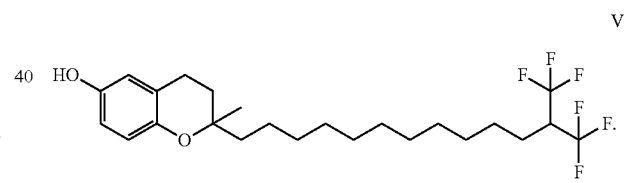

6. A pharmaceutical composition comprising one or more compounds of any one of claims 1-5 and a pharmaceutically acceptable excipient.

7. A method of treating lysosomal storage disorder comprising administering to a patient in need thereof a therapeutically effective amount of a pharmaceutical composition of claim 6.

8. The method of claim 7, further comprising the step of administering to said patient a therapeutically effective amount of a cyclodextrin.

9. The method of claim 7, wherein the lysosomal storage disorder is selected from the group consisting of: Niemann Pick Type C (NPC), Wolman, Niemann Pick Type A, Farber, Tay-Sachs, MSIIIB and CLN2 (Batten) diseases.

10. A method for improving mitochondrial ATP production comprising contacting mitochondria with one or more compounds of any one of claims 1-5.

11. The method of claim 10, wherein the treatment substantially increases $Ca^{2+}$ influx to the cells and/or cholesterol exocytosis from cells of a patient.

12. The method of claim 8, wherein the cyclodextrin is hydroxypropylbetacyclodextrin (HPBCD).

13. The method of claim 9, wherein the lysosomal storage disorder is Niemann-Pick disease Type C (NPC).

14. The method of claim 8, wherein the cyclodextrin is hydroxypropylbetacyclodextrin (HPBCD) and the lysosomal storage disorder is Niemann-Pick disease Type C (NPC).

15. The method of claim 7, wherein the administration is intrathecal administration.

16. The method of claim 7, wherein the administration is intravenous administration.

17. The method of claim 7, wherein the lysosomal storage disorder is selected from the group consisting of: Friedreich's ataxia, Kearns-Sayre syndrome (KSS), Myoclonus epilepsy with ragged-red fibers (MERRF), Mitochondrial encephalomyopathy with lactic acidosis and stroke-like episodes (MELAS), Leberhereditary optic neuropathy (LHON), Leigh syndrome, Myoneurogenic gastrointestinal encephalopathy (MNGIE), Pearson syndrome, and Neuropathy, Ataxia, and Retinitis Pigmentosa (NARP).

* * * * *